(12) United States Patent
Summers

(10) Patent No.: US 6,905,336 B2
(45) Date of Patent: Jun. 14, 2005

(54) IMPRESSION SUPPORT SYSTEM FOR DENTAL IMPLANTS

(76) Inventor: Robert Summers, 5513 Haverhill La., Doylestown, PA (US) 18901

( * ) Notice: Subject to any disclaimer, the term of this patent is extended or adjusted under 35 U.S.C. 154(b) by 357 days.

(21) Appl. No.: 10/200,123

(22) Filed: Jul. 23, 2002

(65) Prior Publication Data

US 2004/0018469 A1 Jan. 29, 2004

(51) Int. Cl.$^7$ .............................. A61C 9/00; A61C 8/00
(52) U.S. Cl. ....................................... 433/214; 433/173
(58) Field of Search ................................ 433/172, 173, 433/174, 175, 176, 213, 214

(56) References Cited

U.S. PATENT DOCUMENTS

| | | | |
|---|---|---|---|
| 2,644,231 A | 7/1953 | Brennan | |
| 4,062,119 A | * 12/1977 | Linkow et al. | ............. 433/176 |
| 5,055,047 A | 10/1991 | Names | ........................ 433/214 |
| 5,125,841 A | 6/1992 | Carlsson et al. | ............. 433/213 |
| 5,219,286 A | * 6/1993 | Hader | ......................... 433/172 |
| 6,149,433 A | 11/2000 | Ziegler et al. | .............. 433/214 |
| 6,213,773 B1 | 4/2001 | Gittleman | .................... 433/172 |
| 6,692,254 B1 | * 2/2004 | Kligerman et al. | .......... 433/173 |
| 2003/0108845 A1 | * 6/2003 | Giovannone et al. | ....... 433/173 |

\* cited by examiner

*Primary Examiner*—Cary E. O'Connor
(74) *Attorney, Agent, or Firm*—Gregory J. Gore

(57) ABSTRACT

A dental implant impression confirmation system utilizes one or more telescoping crossbrace members. Each crossbrace links one coping to an adjacent coping. The ends of the telescoping crossbraces include tubular eyelets or collars which each attach to a coping by snap-fit. The crossbraces further include articulated joints at each end to accommodate attachment between copings which are not parallel. The crossbrace members are preferably composed of a semi-rigid material such as plastic which permits resilience of the confirmation system to allow for the withdrawal of the copings from the implants while supplying sufficient rigidity to enhance the accuracy of the impression.

10 Claims, 5 Drawing Sheets

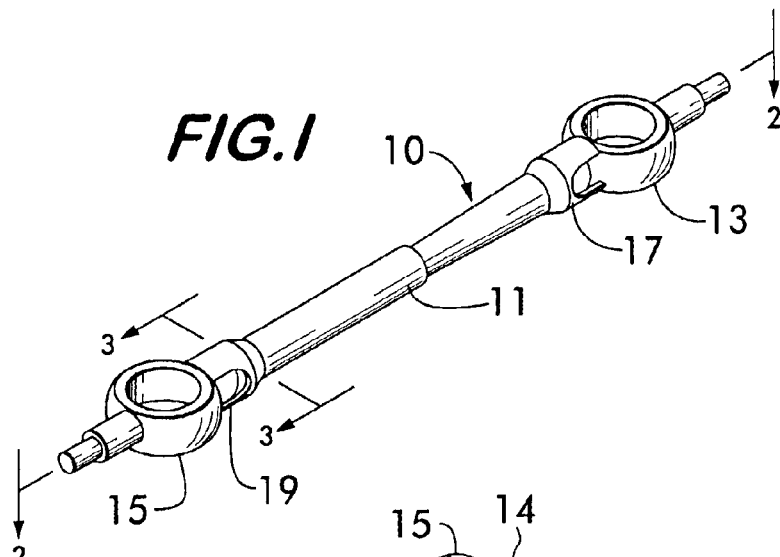
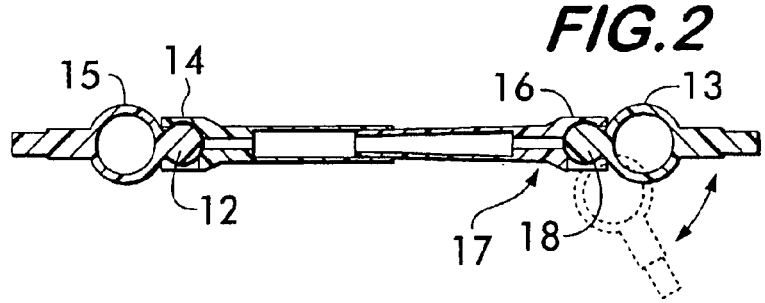
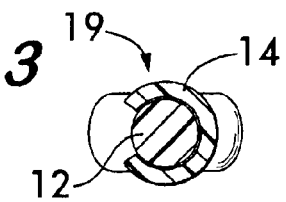
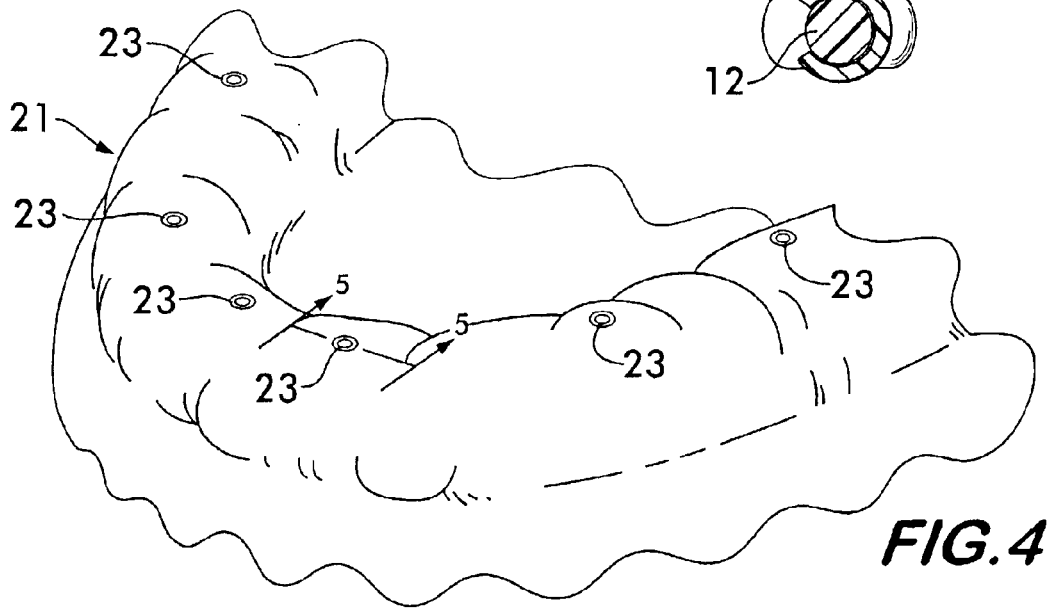

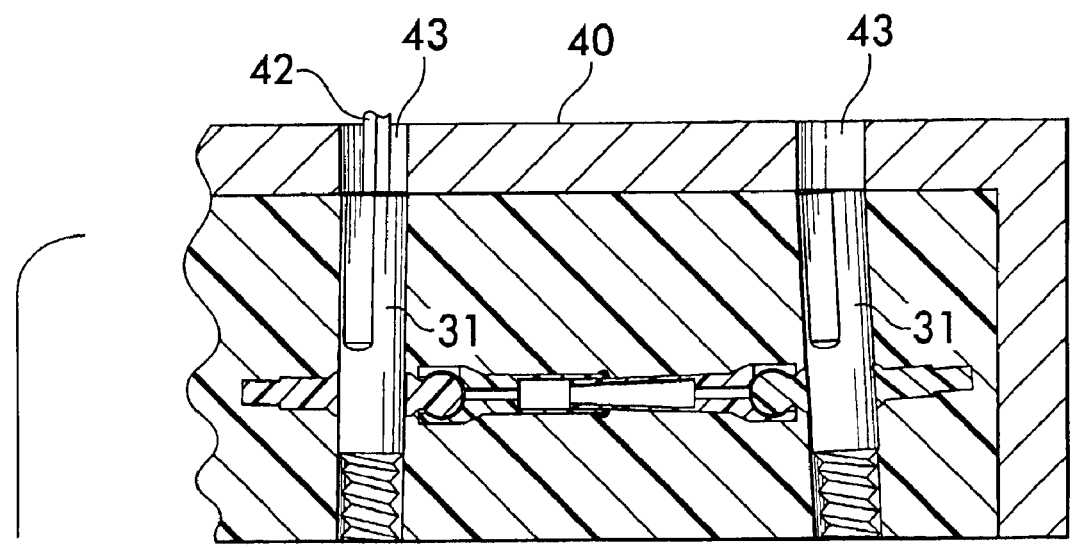
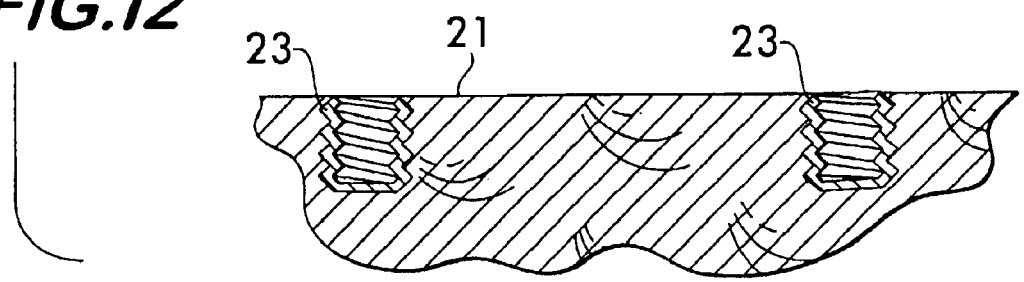
FIG.12

IMPRESSION SUPPORT SYSTEM FOR DENTAL IMPLANTS

FIELD OF THE INVENTION

The present invention relates to structures and methods for forming impressions of dental implants. More specifically, it relates to structures for providing support to the impression material used when taking dental implant impressions to obtain a more accurate model of a patient's mouth and the dental implant components.

BACKGROUND OF THE INVENTION

Dental implants are well known in the dental arts as a means for providing a prosthetic tooth or teeth as an alternative to a fixed bridge or removable dentures. The dental implant procedure begins with first surgically exposing the jaw bone and then drilling the surface of the bone where the prosthetic tooth is to be attached and then inserting an implant. A flap of skin is then sewn over the site and during a healing period that follows, the bone becomes biologically attached to the surface of the implant. Later, after the implant has become thoroughly attached to the bone, the flap is removed. Next, an abutment is screwed onto the implant for ultimate attachment to the prosthetic tooth.

In order to provide the proper shape and orientation of the prosthetic tooth or teeth to be provided, an impression is made of the dental implants and the remaining teeth and gums. In this procedure, a coping or temporary extension is attached at the site of each individual implant by threading the coping into the implant. Next, impression material contained in an impression tray is imposed around the coping and other dental work. After the impression material hardens and copings are unscrewed, the tray is removed. There is a problem, however, because accurate impressions are rarely produced using copings to form the implant impressions. This is a result of distortion of the impression material as the material sets.

In order to solve this problem, a metal impression confirmation system has been devised such as disclosed in U.S. Pat. No. 5,055,047 issued to Names on Oct. 8, 1991. This document discloses the use of a metallic frame comprising individual foundation elements that are attachable to each implant. The frame provides a rigid base around which an impression material may be molded. The molded impression retains dimensional stability by virtue of the rigidity of the frame which is removed from the mouth while still embedded in the hardened impression material. The frame is attached to individual copings by the use of resin bonding, a plurality of metallic wings between adjacent copings to form the frame.

While this solution may provide some advantages, it creates new problems of its own. First, each wing must be individually resin bonded to another structure which requires increased chair time and discomfort to the patient. But more importantly, the metallic frame structure which is the result of the Names process is too rigid to be successfully withdrawn from bores of the implants when the axes of the implants are misaligned, i.e. non-parallel, as often occurs. This makes withdrawal of the impression and coping framework difficult and sometimes even impossible.

Additional patent background art of which the applicant is aware includes U.S. Pat. No. 6,213,773 issued to Gittleman; U.S. Pat. No. 5,125,841 issued to Carlsson et al.; U.S. Pat. No. 6,149,433 issued to Ziegler et al.; and U.S. Pat. No. 2,644,231 issued to Brennan. However, none of the devices disclosed in these patents provides a solution to the problems of dental implant impression confirmation described above.

There is therefore a need in the art for an impression material reinforcement system for use with taking impressions of dental implants which is convenient to use and which supplies the necessary rigidity to the impression material so that accurate impressions of the dental implant copings can be taken.

SUMMARY OF THE INVENTION

In order to solve the problems in the art with dental implant impression confirmation, the present semi-rigid coping reinforcement system has been devised. The invention comprises one or more telescoping crossbrace members which are composed of a semi-rigid material such as plastic. As will be more fully described herein, the crossbraces link each coping to an adjacent coping. The ends of the telescoping crossbraces include tubular eyelets or collars which snap over each coping. A coping intermediate to others will have two separately attached crossbrace members, one over the other. The telescoping feature of the crossbraces permits their length to be adjustable to accommodate for different distances between copings. The crossbraces further include articulated joints at each end to accommodate the attachment between copings which are not parallel. Flexibility of the crossbrace material permits some resilience of the confirmation system to allow for the withdrawal of copings from the implants while at the same time supplying sufficient rigidity to enhance the accuracy of the impression confirmation.

The invention adds to the known procedure the step of applying a plurality of telescoping crossbrace members between the copings. As mentioned above, the crossbrace members are both articulated and telescoping so that they may be adapted to fit onto copings of varying distance and angulation. The ends of the crossbrace members are preliminarily attached to the copings by simple snap-fit that is provided by complementary male/female fit of the plastic crossbrace collars over the coping posts. In this way, all of the coping posts are interconnected by the snap-fit crossbraces. Once the crossbraces are in place, a suitable adhesive is applied to all joints of the crossbraces in order to fix them in place. The specific dimensions and type of plastic are selected to provide the optimal combination of flexibility and rigidity so that the copings may be maintained in their proper position during the impression-taking and curing process while allowing the copings to deflect somewhat so that the completed impression with the embedded copings may be withdrawn from the implants.

More specifically, the applicant has invented an orthodontic coping crossbrace for impression confirmation which comprises a body portion including first and second elongate telescoping members slidably and rotatably fitted together, first and second collars mounted to opposite distal ends of each of the elongate members, and first and second articulated joints coupling the collars to the ends of the elongate members. The collars of the crossbraces are adapted to receive dental implant copings by snap-fit to form a braced coping array in which the copings are affixed to structures implanted into a human jawbone with a plurality of crossbraces each affixed to and extending between each pair of adjacent copings. The crossbraces are further reinforced by an adhesive applied to each collar and joint of the crossbraces. The crossbraces are preferably assembled components all molded from plastic.

It is therefore the main object of the invention to provide a coping impression reinforcement system which is easy to use and which is effective for enhancing the accuracy of dental implant coping impressions. It is a further object of the invention to provide a coping reinforcement system which provides economy of manufacture. Other objectives and advantages will become apparent from the following drawings and description of the preferred embodiment.

BRIEF DESCRIPTION OF THE DRAWINGS

FIG. 1 is a top right front isometric view of the crossbrace of the present invention.

FIG. 2 is a top sectional view taken from FIG. 1 as shown in that figure.

FIG. 3 is a cross-sectional view taken from FIG. 1 as shown in that figure.

FIG. 4 is a top right front isometric view of the human jaw and gum tissue with dental implants.

FIG. 12 is the sectional view shown in FIG. 11 with the copings disengaged from the implants and the impression material separated from the jaw and gum tissue.

DESCRIPTION OF THE PREFERRED EMBODIMENT

Figure 5:
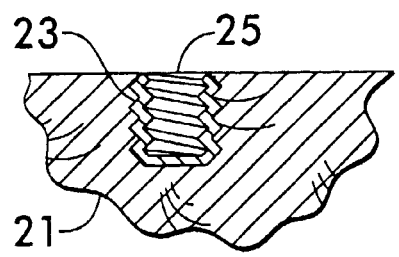
FIG. 5 is a side sectional view of an implant taken from FIG. 4 as shown in that figure.

In use, the present invention generally follows the standard procedure for dental implant impression-taking so a full explanation of all details of this procedure will not be explained herein because it is well-known to those of skill in the art. The sequence of figures that will now be described embody the steps of dental implant coping impression-taking utilizing the reinforcement system of the invention.

Referring now to FIG. 1, a coping crossbrace 10 of the present invention is depicted. Each crossbrace includes a telescoping body member 11 with articulated collars 13 and 15 at opposite ends. Each collar is attached to the main body portion by articulated joints 17 and 19 which in this case are slotted ball-and-socket type joints. As shown in FIG. 2 and as will be readily understood, the various joints of the crossbrace permit the collars to be displaced angularly and linearly with respect to each other to accommodate non-parallel copings. Each articulated joint includes ball-and-socket members 12 and 14 shown adjacent collar 15 and substantially identical members 16 and 18 depicted adjacent collar 13. An alternate collar position afforded by the articulated joint 17 is shown in this figure in phantom lines. FIG. 3 is a sectional view of one of the joints of FIG. 1 showing detail of articulated joint 19 which includes ball element 12 and socket 14.

Figure 6:
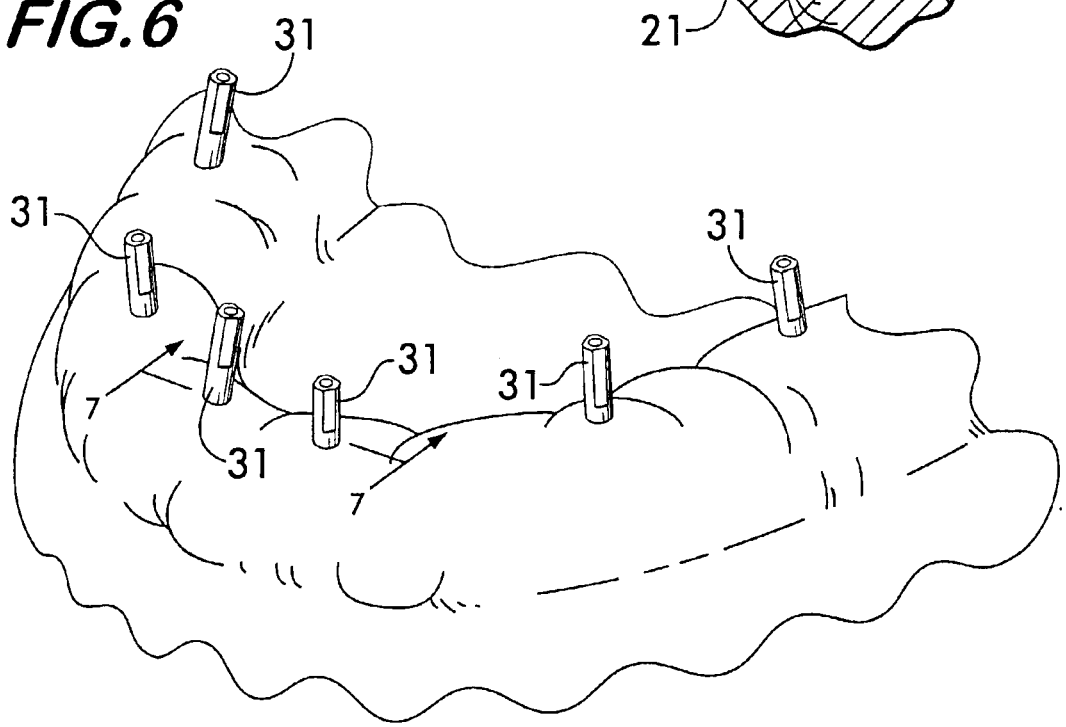
FIG. 6 is a top right front isometric view of the implants of FIG. 4 with dental impression copings installed.
Figure 7:
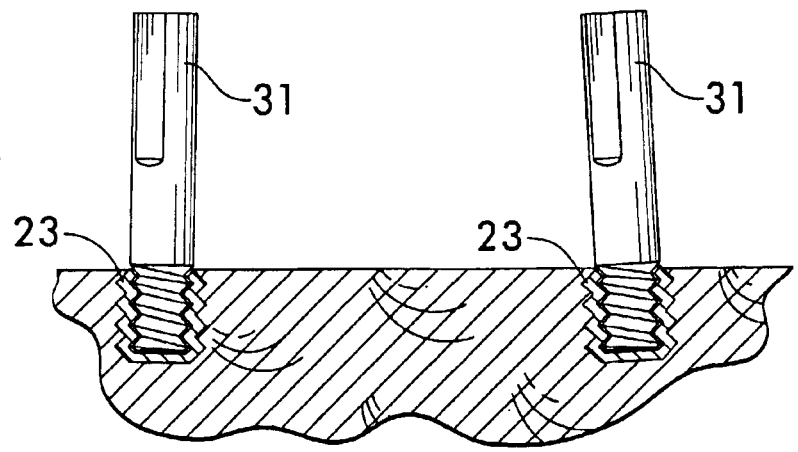
FIG. 7 is a front sectional view taken from FIG. 6 as shown in that figure.

Referring now to FIG. 4, a patient's jawbone and gum structure 21 is shown with implants 23 anchored into the jawbone. As shown in FIG. 5, the implants 23 include internally threaded sockets 25 that are biologically attached to the jawbone 21. Referring to FIG. 6, the next step in the impression-taking process is to screw copings 31 into the implants. As depicted in FIG. 6, it is often the case that the angulation of the implants and copings is non-parallel owing to the shape of the patient's jawbone and the position in which the implant anchors were placed. FIG. 7 shows detail of the copings 31 threaded into the implants 23.

Figure 8:
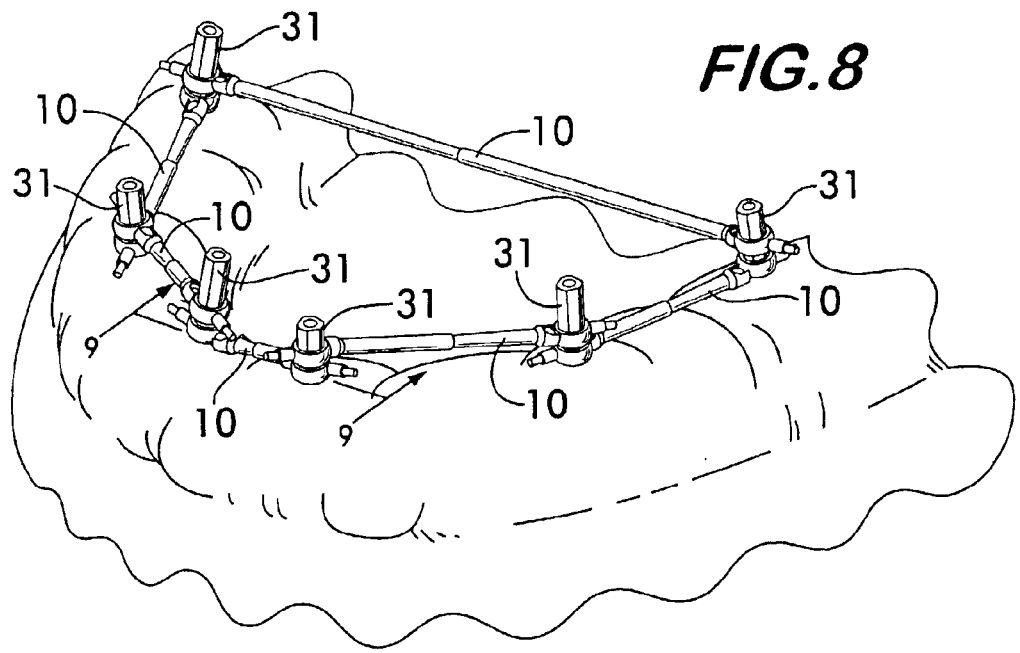
FIG. 8 is a top right isometric view of the coping array shown in FIG. 6 with the crossbraces of the invention installed between adjacent copings.
Figure 9:
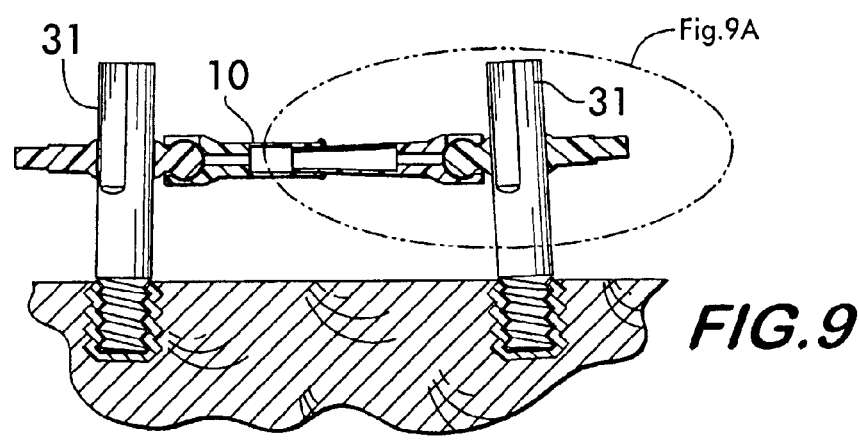
FIG. 9 is a front sectional view of one of the cross members as indicated in FIG. 8.
Figure 9A:
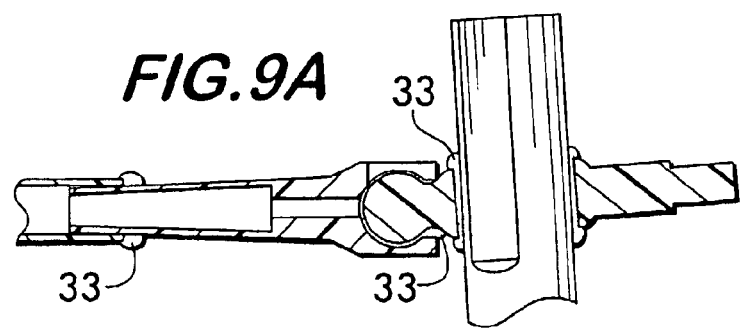

Referring now to FIG. 8, the coping array depicted in FIG. 6 is shown with the crossbraces 10 of the present invention installed between adjacent copings 31. The collars of the ends of the crossbraces are conveniently fitted over the copings preferably by snap-fit. The telescoping and jointed nature of the crossbraces permits them to adapt to the angulation and separation distance of the copings. FIG. 9 shows a sectional view taken from adjacent copings of FIG. 8 which shows placement detail of one of the crossbraces 10 applied between adjacent copings 31. FIG. 9A shows that an adhesive 33 has been applied to all of the crossbraces once they are in place. The adhesive 33 is applied to the collars, the articulated joints, and the telescoping joint in order to form a secure bond between all joints that provides a semi-rigid crossbrace which helps stabilize the alignment of the copings during the taking of the coping impression.

Figure 10:
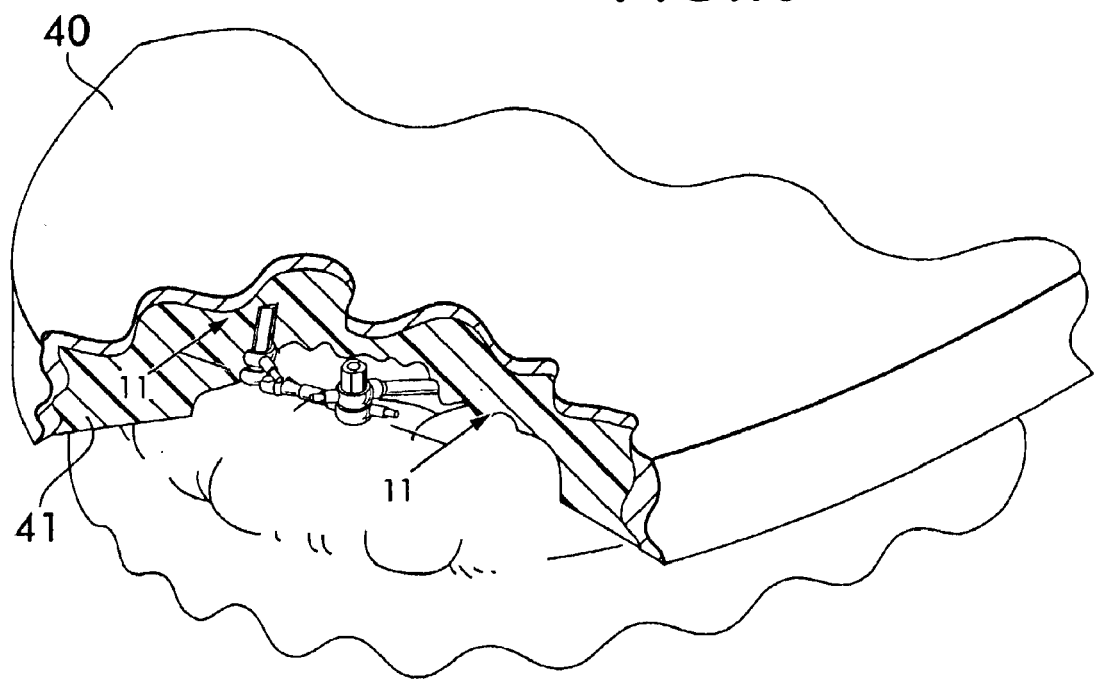
FIG. 10 is a partial cut-away isometric view of the crossbraced coping array shown in FIG. 8 with an impression tray and impression material applied over the crossbraced copings and gum tissue.
Figure 11:
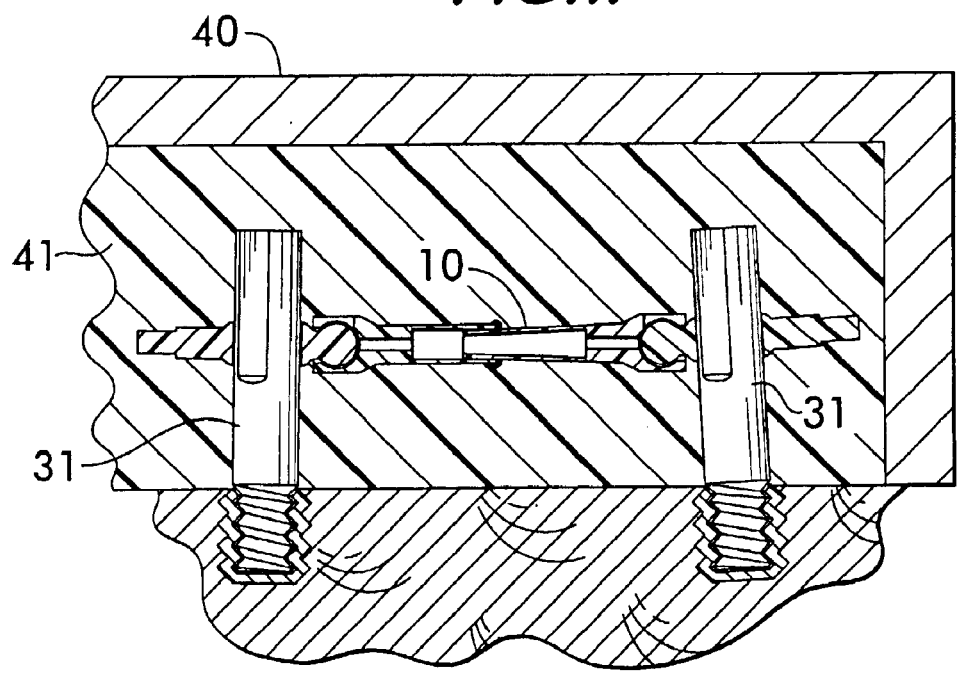
FIG. 11 is a front sectional view taken from FIG. 10 as shown in that figure.

Referring now to FIGS. 10 and 11, in the next step of the procedure a tray 40 including impression material 41 is placed over the crossbraced coping array. As shown in FIG. 11, impression material 41 fully surrounds the copings 31 and crossbraces 10. In this position, the impression material is allowed to cure, thus providing a negative model of the anatomy of the jawbone and gum tissue as well as the location and disposition of the copings, which by their threaded securement to the implants, indicate the exact location and angulation of each implant.

FIG. 12 depicts the same structure shown in FIG. 11 but in the next step of the process. After the impression material has cured, coping access apertures 43 are drilled through the top of tray 40 and through the impression material directly above each coping. The copings 31 are then unscrewed from the implants 23 and the coping array, with crossbrace supports in place, is withdrawn from the jawbone 21. As shown in FIG. 12, tool 42 is used to unscrew the copings from the threaded implants to permit separation of the coping array from the jawbone. This withdrawal of the impression from the jawbone is easily permitted by the present semi-rigid reinforcement system which has some resilience to allow non-parallel copings to deflect slightly to permit upward withdrawal of the impression material and tray.

The invention therefore provides many advantages over the prior art. For example, only a few sizes of telescoping crossbraces are needed for full coverage of all impression cases since each size of crossbrace has length adjustability provided by the telescoping nature of its interfitted parts. Also, the snap-in placement of the crossbraces provides convenience, ease of use, and reduces patient chair time. In addition, the crossbraces may be very inexpensively manufactured since they can be made of resilient molded plastic. Furthermore, because they are plastic, a variety of adhesives may be used to fix the position of the crossbraces and the crossbrace components. The use of molded plastic also allows a wide selection of strength, hardness, flexibility, and resilience.

As an alternate way of employing the invention, telescopic crossbraces without the articulated joints may be used with severely articulated implants by employing a pre-angled abutment to provide a coping orientation that is substantially orthogonal to the bite plane. If this is done for each implant, then the withdrawal of the impression from the array of implants will not require the need for flexure or articulated crossbraces. In this embodiment of the invention, simple non-articulated telescopic crossbraces which may be made from a variety of materials including steel can be employed. Otherwise, the methodology and use is the same as described with regard to the foregoing description of the preferred embodiment in which the crossbraces are preferably made of molded plastic and include articulated joints.

Other modifications may be made which will be obvious to one of skill in the art from the description of the preferred embodiment, however the scope of the applicant's invention should be limited only by the following claims and their legal equivalents.

What is claimed is:

1. A method for taking an impression of an array of dental implant copings comprising the steps of:
    affixing a plurality of copings into dental implants anchored into a patient's jawbone;
    attaching between at least two of said copings a crossbrace member which includes a telescoping body element having opposing ends that include collars that each receive one of said copings by snap-fit;
    applying an adhesive to all joints of said crossbraces;
    placing a dental tray containing impression material around said copings and cross members;
    curing said impression material; and
    removing said tray containing said cross members, copings, and said impression material from said implants.

2. A dental implant coping crossbrace for impression confirmation, comprising:
    a body portion including first and second elongate telescoping members slidably and rotatably fitted together; and
    first and second cylindrical collars mounted to opposite distal ends of each of said elongate members, said collars each being adapted to closely receive a dental implant coping.

3. The crossbrace of claim 2 wherein all of the elements of the crossbrace are composed of molded plastic.

4. A dental implant coping crossbrace for impression confirmation, comprising:
    a body portion including first and second elongate telescoping members slidably and rotatably fitted together;
    first and second collars mounted to opposite distal ends of each of said elongate members, said collars each being adapted to closely receive a dental implant coping; and
    first and second articulated joints coupling said collars to said ends of said elongate members.

5. The crossbrace of claim 4 wherein said collars are adapted to receive dental implant copings by snap-fit.

6. A braced dental implant coping array, comprising:
    a plurality of dental implant copings affixed to structures implanted into a human jawbone; and
    a plurality of crossbraces each affixed to and extending between a pair of adjacent copings wherein said crossbraces are adapted to receive said copings by snap-fit.

7. The dental coping array of claim 6 wherein said crossbraces comprise a pair of interfitting elongate telescoping members.

8. The dental coping array of claim 6 wherein the crossbraces include collars at each end for receiving the copings to which they are attached by snap-fit.

9. The array of claim 7 further including two articulated joints, each joint coupling each of said members to one of said collars.

10. The array of claim 9 wherein the collars are secured to the copings by an adhesive.

* * * * *